(12) United States Patent
Sakai

(10) Patent No.: US 9,194,821 B2
(45) Date of Patent: Nov. 24, 2015

(54) X-RAY COMPUTED TOMOGRAPHY APPARATUS

(71) Applicants: KABUSHIKI KAISHA TOSHIBA, Tokyo (JP); TOSHIBA MEDICAL SYSTEMS CORPORATION, Otawara-Shi, Tochigi-Ken (JP)

(72) Inventor: Satoshi Sakai, Otawara (JP)

(73) Assignees: KABUSHIKI KAISHA TOSHIBA, Tokyo (JP); TOSHIBA MEDICAL SYSTEMS CORPORATION, Otawara-Shi (JP)

( * ) Notice: Subject to any disclaimer, the term of this patent is extended or adjusted under 35 U.S.C. 154(b) by 56 days.

(21) Appl. No.: 13/797,647

(22) Filed: Mar. 12, 2013

(65) Prior Publication Data

US 2013/0259189 A1 Oct. 3, 2013

(30) Foreign Application Priority Data

Mar. 29, 2012 (JP) ................................. 2012-078376

(51) Int. Cl.
*G01N 23/04* (2006.01)
*A61B 6/02* (2006.01)
*A61B 6/03* (2006.01)
*A61B 6/00* (2006.01)

(52) U.S. Cl.
CPC .............. *G01N 23/046* (2013.01); *A61B 6/027* (2013.01); *A61B 6/032* (2013.01); *A61B 6/54* (2013.01); *A61B 6/46* (2013.01); *A61B 6/481* (2013.01); *A61B 6/586* (2013.01); *G01N 2223/419* (2013.01)

(58) Field of Classification Search
CPC ........ A61B 6/032; A61B 6/027; A61B 6/488; A61B 6/5235; A61B 6/54; A61B 6/542
USPC ....................................................... 378/4, 62
See application file for complete search history.

(56) References Cited

U.S. PATENT DOCUMENTS

| | | | | |
|---|---|---|---|---|
| 5,627,868 | A | * | 5/1997 | Nobuta et al. .................... 378/19 |
| 6,449,337 | B1 | * | 9/2002 | Honda et al. ................... 378/117 |
| 2004/0114706 | A1 | | 6/2004 | Ikeda et al. |
| 2006/0274878 | A1 | * | 12/2006 | Hsieh et al. ........................ 378/8 |

(Continued)

FOREIGN PATENT DOCUMENTS

| | | |
|---|---|---|
| CN | 1488317 A | 4/2004 |
| CN | 1561915 A | 1/2005 |

(Continued)

OTHER PUBLICATIONS

Chinese Office Action with its English translation for Chinese Application No. 201310092952.6 mailed on Nov. 27, 2014.

*Primary Examiner* — Hoon Song
(74) *Attorney, Agent, or Firm* — Yoshida & Associates, LLC

(57) ABSTRACT

According to one embodiment, an X-ray computed tomography apparatus includes a rotating frame rotatably supporting an X-ray tube and an X-ray detector detecting X-rays transmitted through an object on a top, a plan storage unit storing a plan for sequentially executing scans to acquire projection data sets with rotation of the rotating frame, a scan information storage unit storing scan information including projection data sets, and a scan control unit determining positions of the rotating frame and the top based on the plan and the scan information when the plan is interrupted and resuming at least one of the plurality of scans in the plan.

6 Claims, 6 Drawing Sheets

(56) References Cited

U.S. PATENT DOCUMENTS

| | | |
|---|---|---|
| 2007/0076852 A1 | 4/2007 | Ishikawa et al. |
| 2009/0202035 A1 | 8/2009 | Tsukagoshi |
| 2010/0135454 A1 * | 6/2010 | Noo .................................. 378/9 |
| 2011/0150173 A1 | 6/2011 | Shinno |

FOREIGN PATENT DOCUMENTS

| | | |
|---|---|---|
| CN | 1943514 A | 4/2007 |
| CN | 101502422 A | 8/2009 |
| CN | 102100564 A | 6/2011 |
| CN | 102711619 A | 10/2012 |
| JP | 06-154204 | 6/1994 |
| JP | 2000-116634 A | 4/2000 |
| JP | 2000-116642 A | 4/2000 |
| JP | 2002-360558 A | 12/2002 |
| JP | 4080725 B2 | 5/2003 |
| JP | 2009-160270 A | 7/2009 |
| JP | 2010-207645 A | 9/2010 |

* cited by examiner

| No. | Start | Start time | Pause duration | Start position | End position | Mode | Number of scans | Speed (Total sec) | Imaging slice thickness (mm) | kV | mA | --- |
| --- | --- | --- | --- | --- | --- | --- | --- | --- | --- | --- | --- | --- |
| 1 | P | *** | 0.0 | 200.0 | 200.0 | S&V | 1 | 0.5(0.5) | 1.0(4.0) | 120 | 300 | --- |
| 2 | P | *** | 0.0 | 0.0 | 200.0 | Helical | 1 | 0.5(5.9) | 0.5(32.0) | 120 | 300 | --- |
| 3 | P | *** | 0.0 | 204.0 | 204.0 | RealPrep | *** | 0.5(52.0) | 1.0(4.0) | 120 | 50 | --- |
| 4 | A | 01:00.0 | *** | 204.0 | 364.0 | Volume | 1 | 0.5(0.5) | 0.5(160.0) | 120 | 300 | --- |
| 5 | P | *** | 0.0 | 204.0 | 524.0 | Volume | 2 | 0.5(1.0) | 0.5(160.0) | 120 | 300 | --- |

Plan setting window 51

FIG. 2

Plan setting window 51a

| No. | Start | Start time | Pause duration | Start position | End position | Mode | Number of scans | Speed (Total sec) | Imaging slice thickness (mm) | kV | mA | |
|---|---|---|---|---|---|---|---|---|---|---|---|---|
| 1 | P | *** | 0.0 | 200.0 | 200.0 | S&V | 1 | 0.5(0.5) | 1.0(4.0) | 120 | 300 | --- |
| 2 | P | *** | 0.0 | 0.0 | 200.0 | Helical | 1 | 0.5(5.9) | 0.5(32.0) | 120 | 300 | --- |
| 3 | P | *** | 0.0 | 204.0 | 204.0 | RealPrep | *** | 0.5(52.0) | 1.0(4.0) | 120 | 50 | --- |
| 4 | A | 01:00.0 | *** | 204.0 | 364.0 | Volume | 1 | 0.5(0.5) | 0.5(160.0) | 120 | 300 | --- |
| 5 | P | *** | 15.0 | 204.0 | 524.0 | Volume | 2 | 0.5(1.0) | 0.5(160.0) | 120 | 300 | --- |

F I G. 6

X-RAY COMPUTED TOMOGRAPHY APPARATUS

CROSS-REFERENCE TO RELATED APPLICATIONS

This application is based upon and claims the benefit of priority from Japanese Patent Application No. 2012-078376, filed Mar. 29, 2012, the entire contents of which are incorporated herein by reference.

FIELD

Embodiments described herein relate generally to an X-ray computed tomography apparatus.

BACKGROUND

An X-ray computed tomography (to be referred to as a CT hereinafter) apparatus includes an X-ray tube which generates X-rays, an X-ray detector which detects X-rays, a movable top on which an object is placed, and an image processing unit which scans the object placed on the top with X-rays while rotating the X-ray tube and the X-ray detector and generates image data by reconstructing the projection data acquired by this scan.

An X-ray CT apparatus has scan modes, e.g., a scan mode of continuously acquiring projection data by irradiating an object with X-rays while moving the top and a scan mode of acquiring projection data by irradiating the object with X-rays while stopping the top. The operator sets a scan mode in accordance with an examination. When executing a plurality of scans in an examination, an operator sets a plan for executing the plurality of scans. There is known an expert plan which allows to sequentially execute the plurality of scans based on the set plan.

If, however, system down occurs in the X-ray CT apparatus due to a power failure or the like in the process of executing scans based on the expert plan, it is necessary to redo from the first scan. This leads to an increase in the exposure dose on the object.

BRIEF DESCRIPTION OF THE DRAWINGS

FIG. 2 is a view showing an example of the plan setting window displayed on a display unit according to the embodiment;

FIG. 6 is a view showing a plan setting window in which a pause duration is set for the fifth scan according to the embodiment.

DETAILED DESCRIPTION

In general, according to one embodiment, an X-ray computed tomography apparatus includes a rotating frame, a plan storage unit, a scan information storage unit, and a scan control unit. The rotating frame rotatably supports an X-ray tube and an X-ray detector. The X-ray tube generates X-rays. The X-ray detector detects the X-rays transmitted through an object on a top. The plan storage unit stores a plan for sequentially executing a plurality of scans to acquire a plurality of projection data sets with rotation of the rotating frame. The scan information storage unit stores scan information including the plurality of projection data sets. The scan control unit determines a position of the rotating frame and a position of the top based on the plan and the scan information when the plan is interrupted, and resumes at least one of the plurality of scans in the plan.

The embodiment will be described below with reference to the accompanying drawings.

Figure 1:
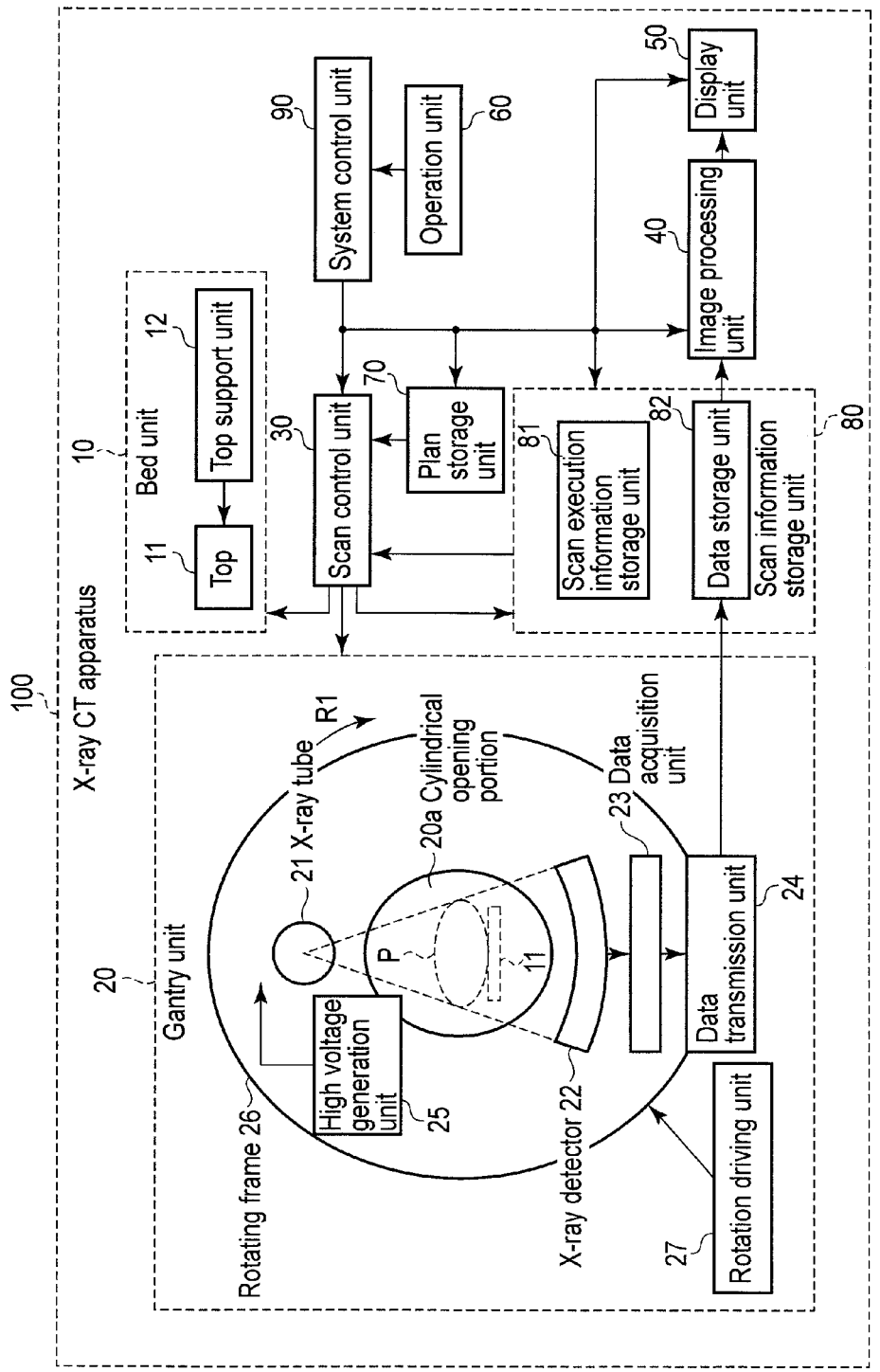
FIG. 1 is a view showing the arrangement of an X-ray CT apparatus according to an embodiment.

FIG. 1 is a view showing the arrangement of an X-ray CT apparatus according to the embodiment. An X-ray CT apparatus 100 includes a bed unit 10 on which an object P is movably placed, a gantry unit 20 which acquires projection data by irradiating the object P placed on the bed unit 10 with X-rays, and a scan control unit 30 which controls the bed unit 10 and the gantry unit 20 to execute scans to acquire projection data.

The X-ray CT apparatus 100 includes an image processing unit 40 which generates image data based on the projection data acquired by the gantry unit 20, a display unit 50 which displays the image data generated by the image processing unit 40, a plan setting window for setting a plan which allows to sequentially execute a plurality of scans, and the like, an operation unit 60 which performs, for example, input operation for setting a plan, and a plan storage unit 70 which stores the plan set/input by the operation unit 60.

The X-ray CT apparatus 100 further includes a scan information storage unit 80 which stores scan information including the projection data set obtained by respective scans sequentially executed based on the plan stored in the plan storage unit 70, and a system control unit 90 which comprehensively controls the scan control unit 30, the image processing unit 40, the display unit 50, the plan storage unit 70, and the scan information storage unit 80.

The bed unit 10 is disposed near the front side of the gantry unit 20 and includes a top 11 on which the object P is placed and a top support unit 12 which supports the top 11 so as to allow it to be movable in the vertical direction and the longitudinal direction. The top support unit 12 moves the top 11 in the longitudinal direction and stops it at a position where the gantry unit 20 can irradiate a morbid region of the object P with X-rays.

The gantry unit 20 includes a cylindrical opening portion 20a extending through a portion between the front side and the back side. The gantry unit 20 includes an X-ray tube 21 which irradiates X-rays on the object P which is moved into the opening portion 20a upon movement of the top 11 of the bed unit 10 in the longitudinal direction, an X-ray detector 22 which is disposed so as to face the X-ray tube 21 through the opening portion 20a and detects the X-rays transmitted through the object P, and a data acquisition unit 23 which acquires a projection data set based on the signal detected by the X-ray detector 22.

The gantry unit 20 includes a data transmission unit 24 which outputs the projection data set acquired by the data acquisition unit 23 to the image processing unit 40, a high voltage generation unit 25 which generates a high voltage to be applied to the X-ray tube 21, a rotating frame 26 which holds the X-ray tube 21, the X-ray detector 22, the data acquisition unit 23, the data transmission unit 24, and the high voltage generation unit 25 so as to allow them to rotate around the object P, and a rotation driving unit 27 which rotates/drives the rotating frame 26 in the arrow R1 direction at a constant rotational speed.

The X-ray tube 21 generates X-rays upon receiving a high voltage applied from the high voltage generation unit 25. The X-ray tube 21 irradiates the object P placed on the top 11 with X-rays while rotating around the object P. The X-ray detector 22 is disposed in an arcuated form in the rotating direction (channel direction). The X-ray detector 22 includes a plurality of X-ray detection elements which are arrayed a matrix pattern in the channel direction and in the rotation axis direction (slice direction) of the rotating frame 26 and convert X-rays into fluorescence and photoelectric conversion elements which convert fluorescence into electrical signals. The X-ray detector 22 detects the X-rays transmitted through the object P and converts the X-rays into electrical signals while rotating around the object P, and outputs the converted signals to the data acquisition unit 23 for each view angle rotation of the rotating frame 26.

The data acquisition unit 23 includes an electronic circuit board including an amplification circuit and an analog/digital conversion circuit. The data acquisition unit 23 is disposed on the outer circumference of the X-ray detector 22. The data acquisition unit 23 acquires a projection data set corresponding to one view by amplifying the signal obtained from the X-ray detector 22 for each rotation of the rotating frame 26 corresponding to, for example, a view angle of 1° and converting the signal from an analog format to a digital format. The data acquisition unit 23 outputs the acquired projection data set to the data transmission unit 24.

The data transmission unit 24 includes a pair of transmission/reception units which perform transmission and reception by, for example, an optical communication means. The data transmission unit 24 then outputs the projection data set acquired by the data acquisition unit 23 to the scan information storage unit 80. The data transmission unit 24 also outputs a control signal from the scan control unit 30 to each unit held on the rotating frame 26.

The rotating frame 26 holds the X-ray tube 21, the X-ray detector 22, the data acquisition unit 23, the data transmission unit 24, and the high voltage generation unit 25 and rotates each held unit in the R1 direction by driving by the rotation driving unit 27.

The scan control unit 30 controls the bed unit 10 and the gantry unit 20 based on the plan saved in the plan storage unit 70. The scan control unit 30 sequentially executes the respective scans to acquire a predetermined number of projection data sets which can generate image data by X-ray irradiation over an angle larger than the view angle (for example, during one rotation of the rotating frame 26). The scan control unit 30 also causes the scan information storage unit 80 to store the information of each scan to be executed based on the plan stored in the plan storage unit 70.

In addition, if a scan (plan) stops in the process of executing the respective scans based on the plan stored in the plan storage unit 70 due to system down such as power failure, the scan control unit 30 resumes the scan by starting X-ray irradiation from a position including the halt positions of the rotating frame 26 and top 11 when the scan has stopped, based on the plan stored in the plan storage unit 70 and the scan information stored in the scan information storage unit 80 until the stoppage of the scan.

In the "S & V" (scan & view) mode, the scan control unit 30 executes an S & V scan to acquire a plurality of projection data sets which can generate two-dimensional image data by performing X-ray irradiation during one rotation of the rotating frame 26 of the gantry unit 20 while stopping the top 11 of the bed unit 10.

In the "Helical" mode, the scan control unit 30 moves the top 11 of the bed unit 10 in the longitudinal direction during rotation of the rotating frame 26 and executes a helical scan to acquire a plurality of projection data sets which can generate a plurality of two-dimensional image data or three-dimensional image data by X-ray irradiation while moving the top 11.

In the "RealPrep" mode, the scan control unit 30 executes a RealPrep scan (specific scan) to acquire a plurality of projection data sets for generating a plurality of two-dimensional image data in a time-series manner, which indicate changes in contrast medium concentration in a region of interest of the object P, by X-ray irradiation during rotation of the rotating frame 26 while stopping the top 11 on which the object P administered with a contrast medium is placed. In this mode, the scan control unit 30 terminates the scan when the CT value of the region of interest of the image data generated by the acquisition of projection data sets reaches a threshold within a preset maximum time or the maximum time elapses before the CT value reaches the threshold.

In the "Volume" mode, the scan control unit 30 executes a volume scan to acquire a plurality of projection data sets which can generate three-dimensional image data by X-ray irradiation during one rotation of the rotating frame 26 while stopping the top 11.

The image processing unit 40 generates two-dimensional or three-dimensional image data by performing reconstruction processing for a plurality of projection data saved in the scan information storage unit 80. The image processing unit 40 outputs the generated image data to the display unit 50.

The operation unit 60 includes input devices such as a keyboard, trackball, joystick, mouse, scan start button, and scan resume button. The operation unit 60 inputs scan conditions for setting a plan, a scan start instruction to start a scan, and a start time when the next scan starts in accordance with the input of the scan start instruction. The operation unit 60 inputs a pause duration by which the start time of the scan is delayed in accordance with the input of a scan start instruction, the maximum time during which X-rays are irradiated in accordance with the input of the scan start instruction, a scan resume instruction to resume a scan which has stopped midway due to system down after the input of the scan start instruction.

The plan storage unit 70 stores the plan set in accordance with the input of scan conditions from the operation unit 60. In this case, a plan is used to sequentially execute the respective scans to acquire a plurality of projection data which can generate image data by X-ray irradiation during rotation of the rotating frame 26 of the gantry unit 20.

The scan information storage unit 80 includes a scan execution information storage unit 81 which stores scan execution information which can be obtained by each scan executed based on the plan stored in the plan storage unit 70 and a data storage unit 82 which stores the projection data set obtained from the gantry unit 20 by each scan.

The scan execution information storage unit 81 includes a nonvolatile memory such as a flash memory, which stores the start input time when a scan start instruction was input from the operation unit 60, the scan start time when each scan started, and the scan end time when each scan was terminated. The scan execution information storage unit 81 stores a skip time which is a time when a scan skip instruction to abort a given scan midway is input from the operation unit 60 and information about the position indicated by the angle of the rotating frame 26 and the position of the top 11 immediately before system down. The scan execution information storage unit 81 also stores the downtime which is a time immediately before system down and the resume instruction input time when an instruction to resume a scan was input from the operation unit 60.

The data storage unit 82 includes a large-capacity magnetic disk and an optical disk. The data storage unit 82 stores a plurality of projection data sets acquired by the respective scans in chronological order in association with identifiable view IDs and scan IDs identifying the scans when the projection data sets were acquired.

Since acquired projection data sets are stored in the data storage unit 82 in association with scan IDs and view IDs, when a scan stops midway due to system down, the scan control unit 30 can search for the number of projection data sets acquired until the stoppage of a stopped scan and a scan ID and view ID which are associated with the latest projection data set in the acquired projection data sets. This allows the scan control unit 30 to calculate the position of the top 11 and the position of the rotating frame 26 of the gantry unit 20 when a scan stopped midway due to system down.

The system control unit 90 includes a CPU and comprehensively controls the overall system including the scan control unit 30, the image processing unit 40, the display unit 50, the plan storage unit 70, and the scan information storage unit 80 based on the input information input from the operation unit 60. The system control unit 90 causes the scan control unit 30 to execute a scan by comprehensively controlling the overall system. The system control unit 90 causes the image processing unit 40 to generate and display image data.

An example of the operation of the X-ray CT apparatus 100 will be described below with reference to FIGS. 1, 2, 3, 4, 5, 6, and 7.

The operator operates the operation unit 60 to display a plan setting window on the display unit 50. The operator then performs input operation to set a plan which executes, for example, five scans to examine the object P. At this time, the system control unit 90 causes the plan storage unit 70 to store the plan set/input from the operation unit 60. The system control unit 90 causes the display unit 50 to display the plan setting window in which the plan for the five scans is set.

FIG. 2 is a view showing an example of the plan setting window displayed on the display unit 50.

A plan setting window 51 in FIG. 2 is constituted by the fields arranged in the horizontal direction, including "No.", "start", "start time", "pause duration", "start position", "end position", "mode", "number of scans", "speed (Total sec)", "imaging slice thickness (mm)", "kV", and "mA", and the fields arranged in the vertical direction, including "1", "2", "3", "4", and "5" respectively corresponding to five scans.

Inputting the respective scan conditions from the operation unit 60 will display the following. The first scan conditions are displayed in the respective fields arranged in the horizontal direction in correspondence with the field "1" of "No.". The second scan conditions are displayed in the respective fields arranged in the horizontal direction in correspondence with the field "2" of "No.". The third scan conditions are displayed in the respective fields arranged in the horizontal direction in correspondence with the field "3" of "No.". The fourth scan conditions are displayed in the respective fields arranged in the horizontal direction in correspondence with the field "4" of "No.". The fifth scan conditions are displayed in the respective fields arranged in the horizontal direction in correspondence with the field "5" of "No.".

When the operator inputs a scan start instruction by operating the start button on the operation unit 60, the field "start" corresponding to "1" of "No." displays "P" indicating that the first scan starts. In addition, since the field "start" displays "P", the field "start time" displays "***" indicating the unnecessity of any setting. The field "pause duration" displays "0.0" indicating that the pause duration by which the start time of the first scan is delayed in accordance with the input of a scan start instruction is 0 sec.

The fields of "start position" and "end position" corresponding to "1" of "No." display "200.0" indicating the position of the top 11 in the longitudinal direction at the time of the start of the scan and at the time of the end of the scan. The field "mode" displays "S & V" indicating that this scan is an S & V scan. The field "number of scans" displays "1" indicating that the number of scans is 1.

The field "speed (Total sec)" corresponding to "1" of "No." displays "0.5 (0.5)" indicating that the rotational speed of the rotating frame 26 is 1 rotation/0.5 sec and the total X-ray irradiation time during rotation of the rotating frame 26 is 0.5 sec. The field "imaging slice thickness (mm)" displays "1.0 (4.0)" indicating that X-rays are detected by using X-ray detection elements of the X-ray detector 22, each having a size of 1.0 mm, arranged in four columns in the slice direction.

In the first scan, therefore, the apparatus starts X-ray irradiation at the initial position of the rotating frame 26 and the position "200.0" of the top 11 as the first scan start position in accordance with a scan start instruction from the operation unit 60. At this time, the top 11 is in a halt state. The apparatus irradiates X-rays over 0.5 sec during which the rotating frame 26 makes one rotation from the initial position. The apparatus acquires the first number of projection data sets by executing the S & V scan at the position of the rotating frame 26 upon making one rotation from the start of X-ray irradiation and the position "200.0" of the top 11 as the first scan end position.

When the operator inputs a scan start instruction after the end of the first scan, the field "start" corresponding to "2" of "No." displays "P" indicating that the second scan starts. In addition, the field "start time" displays "***" indicating the unnecessity of any setting. The field "pause duration" displays "0.0" indicating that the pause duration by which the start time of the second scan is delayed in accordance with the input of a scan start instruction is 0 sec.

The field "start position" corresponding to "2" of "No." displays "0.0" indicating the position of the top 11 in the longitudinal direction at the time of the start of the scan. The field "end position" displays "200.0" indicating the position of the top 11 in the longitudinal direction at the time of the end of the scan. The field "mode" displays "Helical" indicating that this scan is a helical scan. The field "number of scans" displays "1" indicating that the number of scans is 1.

The field "speed (Total sec)" corresponding to "2" of "No." displays "0.5 (5.9)" indicating that the rotational speed of the rotating frame 26 is 1 rotation/0.5 sec and the total X-ray irradiation time of the X-ray tube 21 during rotation of the rotating frame 26 is 5.9 sec. The field "imaging slice thickness (mm)" displays "0.5 (32.0)" indicating that X-rays are detected by using X-ray detection elements of the X-ray detector 22, each having a size of 0.5 mm, arranged in 64 columns in the slice direction.

In the second scan, therefore, the apparatus starts X-ray irradiation at the initial position of the rotating frame 26 and the position "0.0" of the top 11 as the second scan start position in accordance with the input of a scan start instruction. At this time, the apparatus irradiates X-rays over 5.9 sec during which the rotating frame 26 makes 11.8 rotations from the initial position. In addition, the top 11 moves from the position "0.0" to the position "200.0". The apparatus acquires the second number of projection data by executing a helical scan at the position of the rotating frame 26 upon making 11.8 rotations and the position "200.0" of the top 11 as the second scan end position.

When the operator inputs a scan start instruction after the end of the second scan, the field "start" corresponding to "3" of "No." displays "P" indicating that the third scan starts. In addition, the field "start time" displays "***" indicating the unnecessity of any setting. The field "pause duration" displays "0.0" indicating that the pause duration by which the start time of the third scan is delayed in accordance with the input of a scan start instruction is 0 sec.

The fields "start position" and "end position" corresponding to "3" of "No." display "204.0" indicating the position of the top 11 in the longitudinal direction at the time of the start of the scan and at the time of the end of the scan. The field "mode" displays "RealPrep" indicating that this scan is a RealPrep scan. In addition, since the field "mode" displays "RealPrep", the field "number of scans" displays "***" indicating the unnecessity of any setting.

The field "speed (Total sec)" corresponding to "3" of "No." displays "0.5 (52)" indicating that the rotational speed of the rotating frame 26 is 1 rotation/0.5 sec and the maximum time of X-ray irradiation during the rotation of the rotating frame 26 in accordance with the input of a scan start instruction is 52 sec. The field "imaging slice thickness (mm)" displays "1.0 (4.0)" indicating that X-rays are detected by using X-ray detection elements of the X-ray detector 22, each having a size of 1.0 mm, arranged in four columns in the slice direction.

In the third scan, therefore, the apparatus starts X-ray irradiation at the initial position of the rotating frame 26 and the position "204.0" of the top 11 as the third scan position in accordance with a scan start instruction from the operation unit 60. The apparatus irradiates X-rays while the top 11 on which the object P administered with a contrast medium is placed stops and the rotating frame 26 rotates. This generates image data while acquiring projection data sets. The apparatus terminates X-ray irradiation at the third scan end position corresponding to the time when the CT value of a region of interest of generated image data reaches a preset threshold within 52 sec after the input of a scan start instruction or the time when 52 sec elapses before the CT value reaches the threshold. The apparatus executes a RealPrep scan as the third scan in the above manner. With this operation, if X-ray irradiation is to be terminated when the CT value reaches the threshold, the apparatus acquires projection data sets smaller in number than three. If X-ray irradiation is to be terminated when 52 sec elapses, the apparatus acquires the third number of projection data sets.

The field "start" corresponding to "4" of "No." displays "A" indicating that the fourth scan starts after the end of the third scan in accordance with the input of a scan start instruction to start the third scan. The field "start time" displays "01:00.0" indicating that the fourth scan starts one min after the input of the scan start instruction to start the third scan. In addition, since the field "start" displays "A", the field "pause duration" displays "***" indicating the unnecessity of any setting.

The fields "start position" and "end position" corresponding to "4" of "No." display "204.0" indicating the position of the top 11 in the longitudinal direction and "204.0" and "364.0" respectively corresponding to one end and the other end of an imaging range of the object P in the slice direction. The field "mode" displays "Volume" indicating that this scan is a volume scan. The field "number of scans" displays "1" indicating that the number of scans is 1.

The field "speed (Total sec)" corresponding to "4" of "No." displays "0.5 (0.5)" indicating that the rotational speed of the rotating frame 26 is 1 rotation/0.5 sec and the total X-ray irradiation time during the rotation of the rotating frame 26 is 0.5 sec. The field "imaging slice thickness (mm)" displays "0.5 (160.0)" indicating that X-rays are detected by using X-ray detection elements of the X-ray detector 22, each having a size of 0.5 mm, arranged in 320 columns in the slice direction.

In the fourth scan, therefore, the apparatus starts X-ray irradiation from a time point when one min elapses since the input of a scan start instruction to start the third scan from the operation unit 60 at the initial angle of the rotating frame 26 and the position "204.0" of the top 11 as the fourth scan start position. The apparatus then irradiates X-rays for 0.5 sec while the top 11 stops at the position "204.0" and the rotating frame 26 makes one rotation. The apparatus terminates X-ray irradiation at the position of the rotating frame 26 upon rotation from the start of X-ray irradiation and the position "204.0" of the top 11 as the fourth scan end position. In this manner, the apparatus executes the volume scan as the fourth scan. The apparatus acquires the fourth number of projection data sets which can generate image data by executing the volume scan.

Note that in contrast examination, the contrast medium concentration in a morbid region such as a blood vessel after administration of a contrast medium into the object P changes with time. If, therefore, it is necessary to obtain image data at an accurate timing, the apparatus starts the fourth scan after the lapse of a start time since the start of the third scan.

The field "start" corresponding to "5" of "No." displays "P" indicating that the fifth scan starts when a scan start instruction is input after the end of the fourth scan. The field "start time" displays "***" indicating the unnecessity of any setting. In addition, the field "pause duration" displays "0.0" indicating that the time (pause duration) by which the start time of the fifth scan is delayed in accordance with the input of a scan start instruction is 0 sec.

The fields "start position" and "end position" corresponding to "5" of "No." display "204.0" indicating the position of the top 11 in the longitudinal direction at the start time of the scan and "204.0" and "524.0" respectively corresponding to one end and the other end of an imaging range in the slice direction. The field "mode" displays "Volume" indicating that this scan is a volume scan. The field "number of scans" displays "2" indicating that the number of scans is 2.

The field "speed (Total sec)" corresponding to "5" of "No." displays "0.5 (1.0)" indicating that the rotational speed of the rotating frame 26 is 1 rotation/0.5 sec and the total X-ray irradiation time during the rotation of the rotating frame 26 is 1.0 sec. The field "imaging slice thickness (mm)" displays "0.5 (160.0)" indicating that X-rays are detected by using X-ray detection elements of the X-ray detector 22, each having a size of 0.5 mm, arranged in 320 columns in the slice direction.

In the fifth scan, therefore, the apparatus starts the first X-ray irradiation at the initial position of the rotating frame 26 and the position "204.0" of the top 11 as the first scan start position in accordance with the input of a scan start instruction to start a scan from the operation unit 60. The apparatus then irradiates X-rays over 0.5 sec while the top 11 stops at the position "204.0" and the rotating frame 26 makes one rotation. The apparatus terminates the first X-ray irradiation at the position of the rotating frame 26 upon making one rotation from the start of X-ray irradiation and the position "204.0" of the top 11 as the first scan end position. In this manner, the apparatus executes the first volume scan. With this operation, the apparatus acquires the fourth number of projection data sets which can generate image data.

After the end of the first volume scan, the top 11 moves in the longitudinal direction and stops at the position "364.0" The apparatus then starts the second X-ray irradiation at the initial position of the rotating frame 26 and the position "364.0" of the top 11 as the second scan start position. The apparatus then irradiates X-rays over 0.5 sec while the top 11 stops and the rotating frame 26 makes one rotation. The apparatus terminates the second X-ray irradiation at the position of the rotating frame 26 upon making one rotation from the start of X-ray irradiation and the position "364.0" of the top 11 as the second scan end position. The apparatus executes the second volume scan in this manner. With this operation, the apparatus acquires the fourth number of projection data sets which can generate image data. With these operations, the apparatus acquires the fifth number of projection data sets, which is twice the fourth number, by the combination of the first and second scans.

Note that the fifth scan may be a dynamic volume scan which continuously executes m (m is a natural number) volume scans. At this time, the number of scans corresponding to "5" of No." in FIG. 2 is m.

Figure 3:
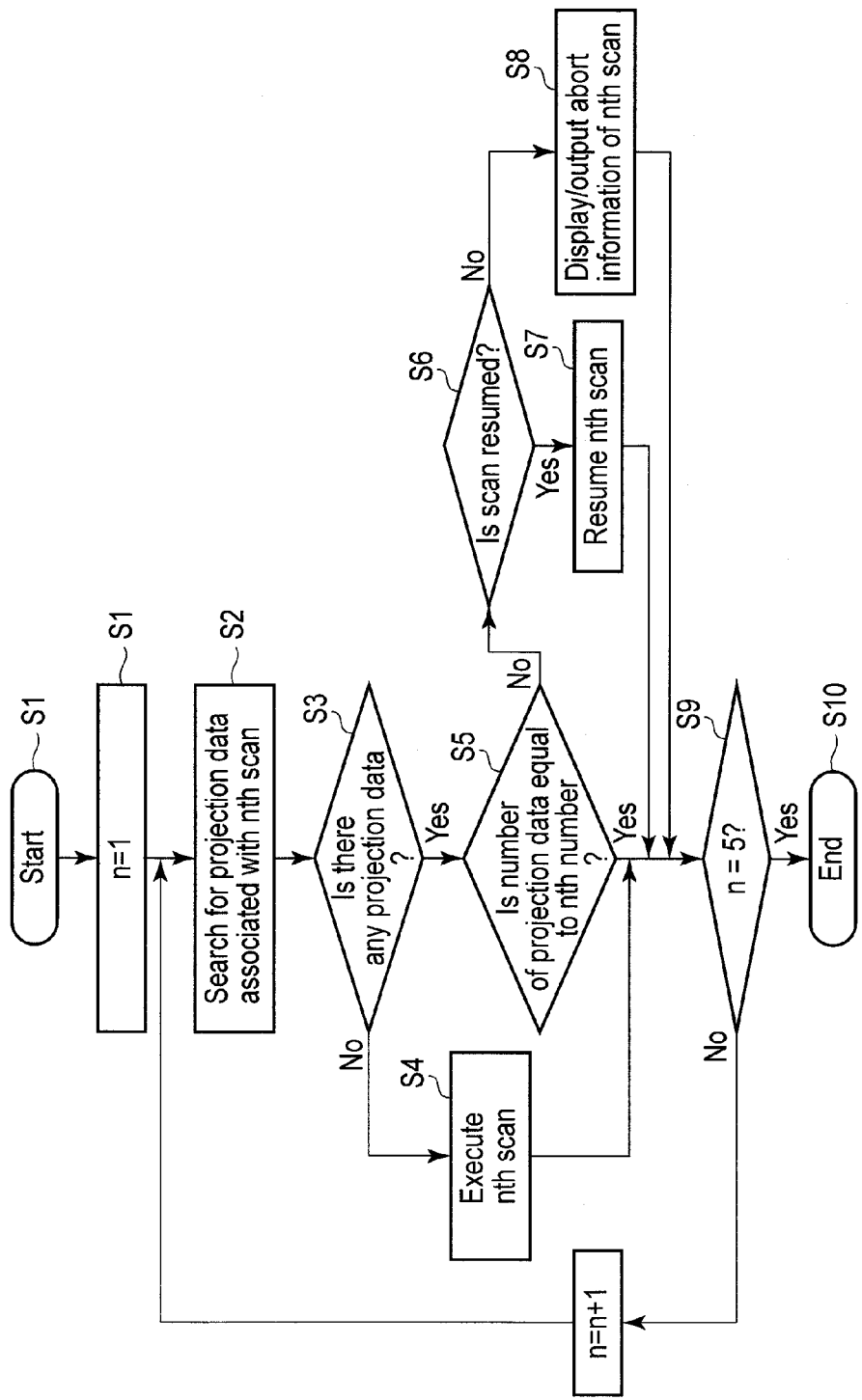
FIG. 3 is a flowchart showing the operation of an X-ray CT apparatus according to the embodiment.

FIG. 3 is a flowchart showing the operation of the X-ray CT apparatus 100.

After the operator sets a plan for examining the object P, the object P is placed on the top 11. The operator then operates the operation unit 60 to move the top 11 to the position "0.0" displayed in the plan setting window 51 in FIG. 2. When the operator inputs a scan start instruction, the X-ray CT apparatus 100 starts operating. When the operator inputs a scan resume instruction from the operation unit 60 upon restarting the apparatus after the occurrence of system down during a scan, the X-ray CT apparatus 100 starts operating (step S1).

The system control unit 90 issues an instruction to resume the scan by controlling the scan control unit 30, the image processing unit 40, the display unit 50, the plan storage unit 70, and the scan information storage unit 80. The scan control unit 30 searches for a projection data set associated with the nth (n=1) scan based on the plan saved in the plan storage unit 70 (step S2).

If the projection data set associated with the nth scan is not stored in the data storage unit 82 (NO in step S3), the system control unit 90 executes the nth scan from the nth scan start position (step S4). The process then shifts to step S9 after the end of the nth scan. If the projection data set associated with the nth scan is stored in the data storage unit 82 (YES in step S3), the process shifts to step S5.

If projection data sets smaller in number than the nth number are stored in the data storage unit 82 (NO in step S5) after YES is determined in step S3, the system control unit 90 determines that the nth scan has stopped midway due to system down. At this time, the process shifts to step S6. If projection data the number of which equals the nth number are stored in the data storage unit 82 (YES in step S5), the system control unit 90 determines that the nth scan is complete. At this time, the process shifts to step S9.

If the number of projection data acquired by the nth scan is smaller than the nth number, the system control unit 90 searches for skip time information in the scan execution information storage unit 81. If skip time information corresponding to the input of a scan skip instruction from the operation unit 60 is stored in the scan execution information storage unit 81, the system control unit 90 determines that the nth scan is complete.

After NO is determined in step S5, the scan control unit 30 determines whether to resume the nth scan, based on the plan stored in the plan storage unit 70 and the scan information saved in the scan information storage unit 80. Upon determining to resume the nth scan (YES in step S6), the scan control unit 30 decides the positions of the rotating frame 26 and top 11 at which X-ray irradiation is to be resumed. The scan control unit 30 resumes the nth scan by starting X-ray irradiation from the decided position (step S7). The scan control unit 30 executes the nth scan in which X-ray irradiation is terminated at the nth scan end position. At this time, the process shifts to step S9 after the end of the nth scan.

When aborting the nth scan (NO in step S6), the scan control unit 30 causes the display unit 50 to display/output abort information of the nth scan (step S8). The process then shifts to step S9.

If n is an integer less than 5 when the nth scan is terminated or aborted (NO in step S9), the process returns to step S2 upon addition of 1 to n. If n is 5 (YES in step S9), the process shifts to step S10.

When the fifth scan is complete after YES is determined in step S9, the system control unit 90 issues a scan end instruction. At this time, the scan control unit 30 stops the top 11 and the rotating frame 26 at the home positions. With this processing, the X-ray CT apparatus 100 terminates the operation (step S10).

The operation in steps S6 to S8 in FIG. 3 will be described in detail next.

Figure 4:
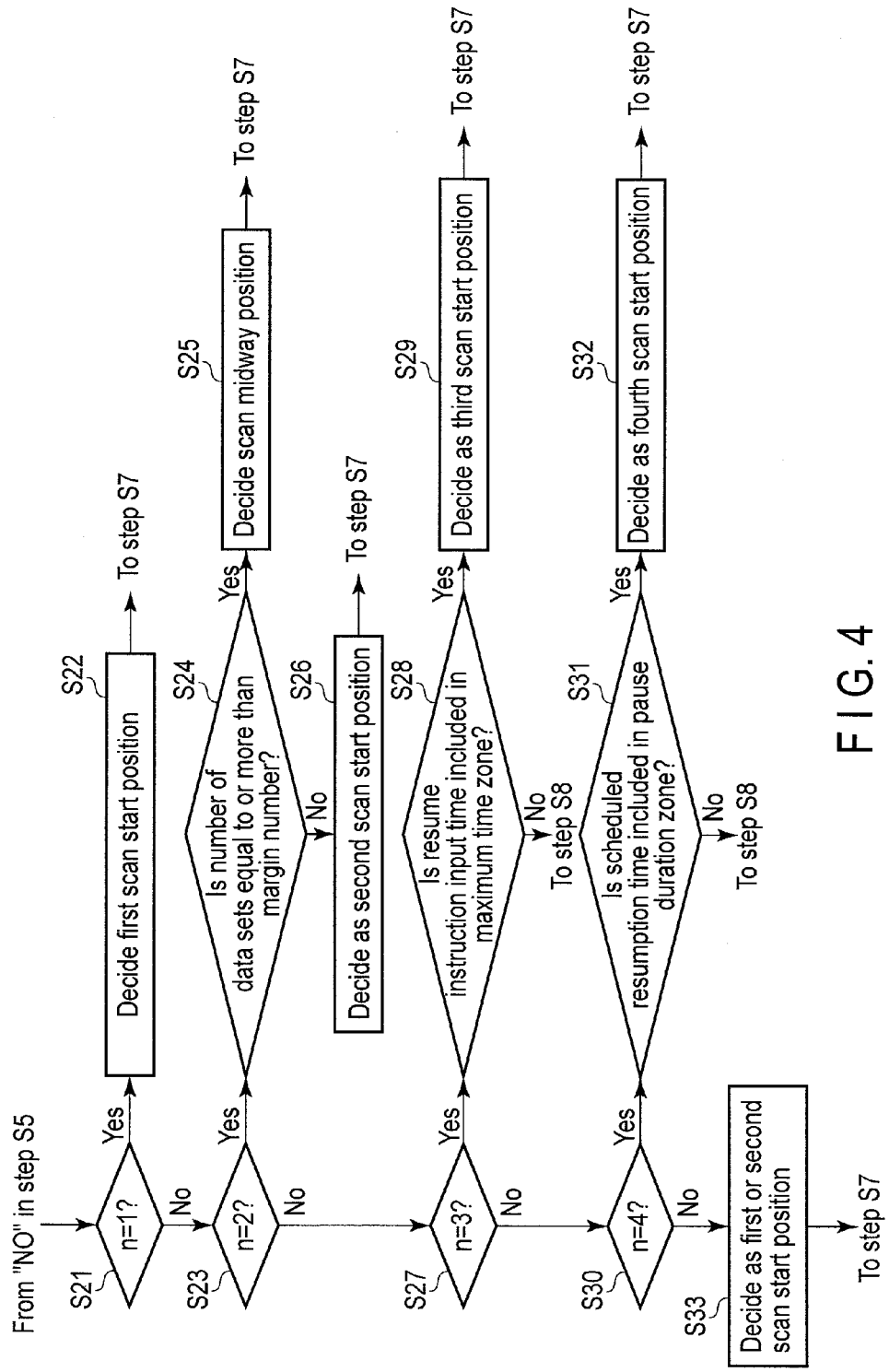
FIG. 4 is a flowchart showing the details of operation in step S6 in FIG. 3.

FIG. 4 is a flowchart showing the details of the operation in steps S6 to S8 in FIG. 3. Step S6 is constituted by steps S21 to S33.

If the scan control unit 30 determines that n is 1 (YES in step S21) after NO is determined in step S5 in FIG. 3, the process shifts to step S22. If n is a positive integer other than 1 (NO in step S21), the process shifts to step S23.

No start or pause duration is set for the first scan in which n is 1. In addition, the first scan is in the S & V scan mode, and the number of scans is 1. If, therefore, the rotating frame 26 stops rotating before making one rotation from the start of X-ray irradiation, the scan control unit 30 determines that it is not possible to generate image data. The scan control unit 30 then decides the positions of the rotating frame 26 and top 11 at which X-ray irradiation is to be resumed as the first scan start position (step S22).

If n is 2 (YES in step S23) after NO is determined in step S21, the process shifts to step S24. If n is a positive integer other than 2 (NO in step S23), the process shifts to step S27.

No start or pause duration is set for the second scan in which n is 2. In addition, the second scan is in the helical scan mode, and the number of scans is 1. If the number of projection data sets saved in the data storage unit 82 by a helical scan until the scan has stopped midway is equal to or more than a margin number (e.g., the number of projection data sets acquired during two rotations of the rotating frame 26) (YES in step S24), the scan control unit 30 decides the positions of the rotating frame 26 and top 11 at which X-ray irradiation is to resume as the positions of the rotating frame 26 and top 11 (scan midway position) when a projection data set tracing back the projection data sets stored in the control processor 28 by the helical scan from the latest projection data set by the margin number has been acquired (step S25).

If the number of projection data sets saved in the data storage unit 82 by the helical scan is less than the margin number (NO in step S24), it is not possible to provide any margin region before the resumption of the scan for the projection data sets acquired until X-ray irradiation has stopped. For this reason, the scan control unit 30 decides the positions of the rotating frame and top (second scan start position) at the above helical scan start time as the resumption position of the helical scan (step S26).

Note that a plurality of projection data sets tracing back from the latest projection data set stored in the data storage unit 82 until the helical scan has stopped by a margin number counted from the latest projection data set become projection data sets in a margin region before resumption. The apparatus resumes the helical scan from a midway position in the scan. Projection data sets equal in number to the margin number which are acquired by the scan at the same positions of the rotating frame 26 and top 11 as those in the margin region before resumption are projection data sets in the margin region after resumption. The image processing unit 40 performs data processing for making the projection data sets in the margin regions before and after the resumption have continuity.

As described above, when a helical scan stops midway, if the number of projection data sets stored in the data storage unit 82 by the helical scan is less than the margin number, the apparatus resumes the helical scan from the second scan start position. This makes it unnecessary to execute any scan before the helical scan, and hence it is possible to reduce the expose dose on the object P. If the number of projection data sets stored in the data storage unit 82 by the helical scan is equal to or more than the margin number, the apparatus resumes the helical scan from a scan midway position. This makes it unnecessary to perform X-ray irradiation from the second scan start position to the scan midway position. It is therefore possible to reduce the exposure dose on the object P.

If n is 3 (YES in step S27) after NO is determined in step S23, the process shifts to step S28. If n is a positive integer other than 3 (NO in step S27), the process shifts to step S30.

If n is 3, no start or pause duration is set for the third scan (specific scan). In addition, the third scan is in the RealPrep scan mode. If the operator inputs a scan resume instruction from the operation unit 60 when the third scan has stopped midway, the scan control unit 30 determines whether it is possible to resume the third scan, based on the scan execution information which is stored in the scan execution information storage unit 81 and includes the resume instruction input time when an instruction to resume the scan is input.

Figure 5:
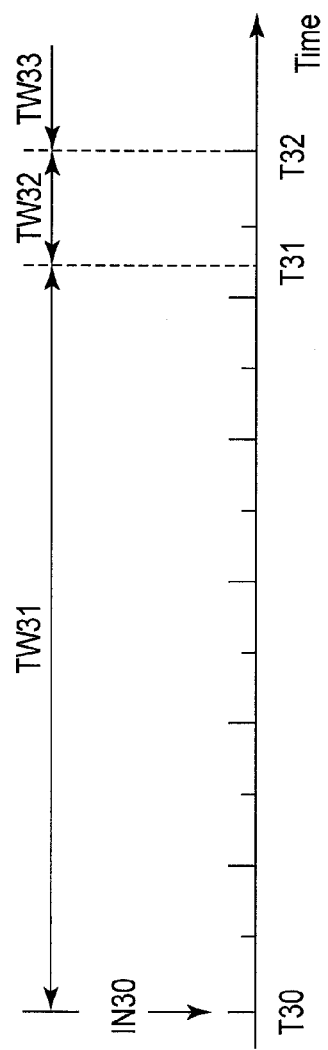
FIG. 5 is a view for explaining the third scan according to the embodiment.

As shown in FIG. 5, if the resume instruction input time is included in TW31 between T30 and T31 (YES in step S28), the scan control unit 30 decides the positions of the rotating frame 26 and top 11 at which X-ray irradiation is to be resumed as the third scan start position (step S29). T30 indicates the start instruction input time when the operator has performed the input operation IN30 for a scan start instruction to start the third scan before system down from the operation unit 60. T31 indicates the scheduled end time at which 52 sec, which is maximum time (X-ray irradiation time), displayed in the field "speed (Total sec)" corresponding to "3" of "No." in the plan setting window 51 has elapsed from start instruction input time T30. TW31 indicates the time interval (maximum time zone TW31) between start instruction input time T30 and scheduled end time T31.

Assume that the positions of the rotating frame 26 and top 11 at which X-ray irradiation is to be resumed are decided as the third scan start position. In this case, when the CT value of a region of interest of image data generated from projection data sets acquired by the third scan before scheduled end time T31 reaches a threshold, the apparatus terminates the third scan. Assume that the positions of the rotating frame 26 and top 11 at which X-ray irradiation is to be resumed are decided as the third scan start position. In this case, when the scan time of the third scan reaches the scheduled end time T31 before the CT value reaches the threshold, the apparatus terminates the third scan.

If the resume instruction input time is a time after scheduled end time T31 (NO in step S28), the apparatus aborts the resumption of the third scan. In addition, the abort information of the third scan is displayed/output onto the display unit 50 (step S8 in FIG. 3).

In the third scan for which the maximum time for limiting an X-ray irradiation time is set, if a resume instruction input time is included in the time zone TW31, it is possible to resume the third scan to start X-ray irradiation from the third scan start position. This makes it unnecessary to execute the first and second scans, and hence it is possible to reduce the exposure dose on the object P. If the resume instruction input time comes after scheduled end time T31, since scheduled end time T31 at which it is necessary to terminate the third scan has elapsed, it is possible to abort the third scan which is unnecessary. This can reduce the exposure dose on the object P.

If n is 4 (YES in step S30) after NO is determined in step S27, the process shifts to step S31. If n is a positive integer other than 4 (NO in step S30), the process shifts to step S33.

In the fourth scan (post scan) in which n is 4, a start time is set. If, therefore, the fourth scan stops midway in the process of executing the fourth scan, when the operator inputs a scan resume instruction from the operation unit 60, the scan control unit 30 calculates margin times such as a time taken for the rotational speed of the rotating frame 26 to become constant and a time taken to move the top 11 to a resumption position in order to resume the fourth scan. For example, a margin time is a time taken to allow the resumption of the fourth scan. The scan control unit 30 then calculates the scheduled resumption time which has elapsed from the resume instruction input time, at which the operator has input a scan resume instruction, by the margin time. The scan control unit 30 determines, based on the scheduled resumption time, whether it is possible to resume the fourth scan.

As shown in FIG. 5, if a scheduled resumption time is included in a pause duration band TW32 between scheduled end time T31 and time T32 which has elapsed from start instruction input time T30 by 1 min displayed in the field "start time" corresponding to "4" in the plan setting window 51 (YES in step S31), the scan control unit 30 decides the positions of the rotating frame 26 and top 11 at which X-ray irradiation is to be resumed as the fourth scan start position (step S32).

In addition, as shown in FIG. 5, if the scheduled resumption time is included in a time zone TW33 after time T32 (NO in step S31), since time T32 at which the fourth scan needs to start has been elapsed, the apparatus aborts the resumption of the fourth scan. In addition, fourth scan abort information is displayed/output onto the display unit 50 (step S8 in FIG. 2).

In this manner, the apparatus starts the fourth scan in accordance with the input of a scan start instruction to start the third scan. That is, if the resume instruction input time is included in the pause duration band TW32, it is possible to execute the fourth scan, which needs to start in accordance with the third scan, from the fourth scan start position at time T32. This makes it unnecessary to execute the associated first to third scans, and hence it is possible to reduce the exposure dose on the object P. If the resume instruction input time is included in the time zone TW33, since time T32 at which the fourth scan needs to start has been reached, it is possible to abort the unnecessary fourth scan. This can reduce the exposure dose on the object P.

No start or pause duration is set for the fifth scan in which n is 5 after NO is determined in step S30. In addition, the fifth scan is in the volume scan mode. The number of fifth scans is 2. The scan control unit 30 therefore calculates the halt position of the fifth scan based on the scan ID and the view ID which are associated with the latest projection data set stored in the data storage unit 82 by the fifth scan. If the calculated halt position is a midway position in the first scan, the scan control unit 30 decides the fifth scan resumption position as the first scan start position. Before the start of the second scan after the end of the first scan or in the process of executing the second scan, the scan control unit 30 decides the fifth scan resumption position as the start position of the second scan (step S33).

As described above, when the fifth scan, i.e., the first scan in the volume scan mode, stops midway, the scan control unit 30 can resume the first volume scan, in which X-ray irradiation starts, at the first scan start position. This makes it unnecessary to execute the first to fourth scans, and hence it is possible to reduce the exposure dose on the object P. Before the start of the second scan after the end of the first scan or when the second scan stops midway, the scan control unit 30 can resume the second volume scan from the second scan start position. This makes it unnecessary to execute the first volume scan again, and hence it is possible to reduce the exposure dose on the object P.

A case in which pause duration is set in the field "pause duration" in the plan setting window 51 will be described next.

FIG. 6 is a view showing a plan setting window 51a in which a pause duration is set for the fifth scan. The plan setting window 51a differs from the plan setting window 51 in FIG. 2 in that the field "pause duration" corresponding to "5" of "No." displays "15.0". The following are the differences from the operation in step S4 in FIG. 3 when the apparatus executes a plurality of scans based on the plan setting window 51a and stops in the process of executing the fifth scan.

When the fifth scan stops midway and the operator inputs a scan resume instruction from the operation unit 60, the scan control unit 30 calculates margin times such as a time taken for the rotational speed of the rotating frame 26 to become constant and a time taken to move the top 11 to a scan resumption position in order to resume the fifth scan. For example, a margin time is a time taken to allow the resumption of the fifth scan. The scan control unit 30 then calculates the scheduled resumption time which has elapsed from the resume instruction input time, at which the operator has input a scan resume instruction, by the margin time. The scan control unit 30 determines, based on the scheduled resumption time and the scan execution information stored in the scan execution information storage unit 81, whether it is possible to resume the fifth scan.

Figure 7:
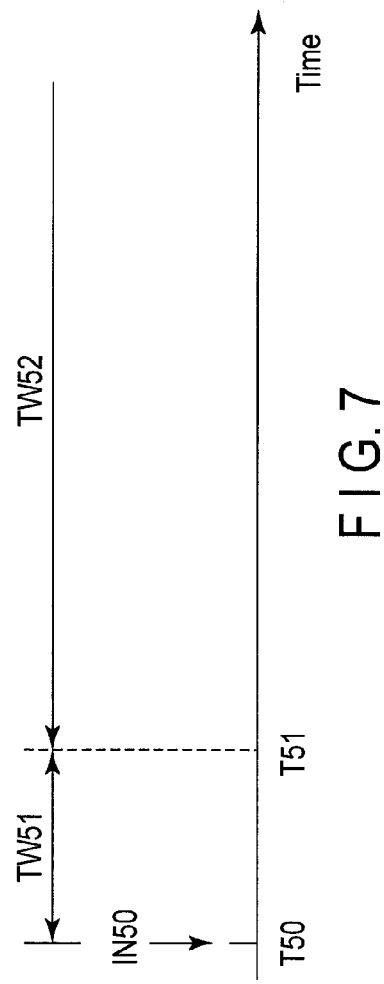
FIG. 7 is a view for explaining the fifth scan for which pause duration is set according to the embodiment.

As shown in FIG. 7, if the scheduled resumption time is included in a time zone TW51 between start instruction input time T50 and scheduled start time T51 which has elapsed from start instruction input time T50 by 15 sec as a pause duration, the scan control unit 30 resumes the fifth scan which starts X-ray irradiation from the first scan start position at scheduled start time T51. Start instruction input time T50 is the time when the operator has performed scan start instruction input operation IN50 to start the fifth scan before system down.

If the scheduled resumption time is included in a time zone TW52 after scheduled start time T51, the scan control unit 30 stops the resumption of the fifth scan. The scan control unit 30 then causes the display unit 50 to display the "execute" and "abort" buttons to prompt the operator to determine whether to execute the fifth scan. If the operator selects/inputs "execute" from the operation unit 60, the scan control unit 30 resumes the fifth scan in a halt state. If the operator selects/inputs "abort" from the operation unit 60, the scan control unit 30 terminates the fifth scan.

As described above, in scanning operation which requires to start a scan after pause duration in accordance with the input of a scan start instruction, if the resume instruction input time is included in the time zone TW51, the scan control unit 30 can resume the fifth scan which starts X-ray irradiation from the first scan start position. This makes it unnecessary to execute the first to fourth scans, and hence it is possible to reduce the exposure dose on the object P. In addition, if the resume instruction input time is included in the time zone TW52, the scan control unit 30 can pause the resumption of the fifth scan which may become unnecessary. This can reduce the exposure dose on the object P.

Note that start time and pause duration settings can be generally applied to any types of scan modes as well as the RealPrep mode and the post scan mode.

According to the above embodiment, the plan storage unit 70 stores a plan which executes the first to fifth scans, and the scan information storage unit 80 can store the scan information obtained by the first to fifth scans executed based on the plan stored in the plan storage unit 70. This makes it possible to, when a scan stops in the process of executing the first to fifth scans, resume the scan which has stopped by starting X-ray irradiation from a position including the halt positions of the rotating frame 26 and top 11 when the corresponding one of the first to fifth scans has stopped, based on the plan stored in the plan storage unit 70 and the scan information stored in the scan information storage unit 80 until the corresponding one of the first to fifth scans has stopped (stopped midway).

In this embodiment, when the second scan stops midway and the number of projection data sets stored in the data storage unit 82 becomes less than the margin number, the apparatus can resume the second scan which starts X-ray irradiation from the second scan start position. This makes it unnecessary to execute the first scan again, and hence it is possible to reduce the exposure dose on the object P. If the number of projection data sets stored in the data storage unit 82 is equal to or more than the margin number, the embodiment can resume the second scan which starts X-ray irradiation from a midway position in the scan. According to the embodiment, it is not necessary to perform X-ray irradiation from the second scan start position to the midway position, and hence it is possible to reduce the exposure dose on the object P.

According to this embodiment, in the third scan for which the maximum time which limits an X-ray irradiation time is set, if a resume instruction input time is included in the maximum time zone TW31 between the start instruction input time T30 and scheduled end time T31, it is possible to resume the third scan which starts X-ray irradiation from the third scan start position. This makes it unnecessary to execute the first and second scans, and hence it is possible to reduce the exposure dose on the object P. In addition, if a resume instruction input time is included in the pause duration band TW32 between scheduled end time T31 and time T32, the resume instruction input time has passed scheduled end time T31 at which it is necessary to terminate the third scan. For this reason, according to the embodiment, it is possible to reduce the exposure dose on the object P by aborting the third scan which is unnecessary.

In addition, in the fourth scan which needs to start after the start time set as a scan condition in accordance with the input of a scan start instruction to start the third scan, if the resume instruction input time is included in the pause duration band TW32, it is possible to execute the fourth scan from the fourth scan start position at time T32. This makes it unnecessary to execute the first to third scans, and hence it is possible to reduce the exposure dose on the object P.

Furthermore, if the first volume scan in the fifth scan stops midway, it is possible to resume the first volume scan at the first scan start position. This makes it unnecessary to execute the first to fourth scans, and hence it is possible to reduce the exposure dose on the object P. In addition, before the start of the second volume scan after the end of the first volume scan or when the second volume scan stops midway, it is possible to resume the second volume scan from the second scan start position. This makes it unnecessary to execute the first volume scan again, and hence it is possible to reduce the exposure dose on the object P.

In addition, in a scan which needs to start after pause duration in accordance with the input of a scan start instruction for which the pause duration in the fifth scan is set, if the resume instruction input time is before scheduled start time T51, it is possible to resume the fifth scan from the first scan start position. This makes it unnecessary to execute the first to fourth scans, and hence it is possible to reduce the exposure dose on the object P. In addition, if the resume instruction input time is after scheduled start time T51, it is possible to stop the resumption of the fifth scan which may be unnecessary. This makes it possible to reduce the exposure dose on the object P.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computed tomography apparatus comprising:
a plan storage unit configured to store a plan for sequentially executing a plurality of scans to acquire a plurality of projection data sets;
a scan information storage unit configured to store scan information including the plurality of projection data sets; and
a scan control unit configured to determine, based on the scan information until an interruption of the scan being executed, a scan interruption position corresponding to a time at which the scan being executed is interrupted and to resume the interrupted scan in the plan from the scan interruption position, wherein at least one of the plurality of scans comprises a first scan and a second scan after the first scan, the first scan and the second scan acquiring the plurality of projection data sets during a stationary state of a top to allow generation of image data, and
the scan control unit is configured to:
calculate a halt position in the first scan and the second scan based on the plurality of projection data sets for the first scan and the second scan that are stored in the scan information storage unit;
if the halt position is in the first scan, determine the position as of start of the first scan as a resumption position and resume the first scan from the resumption position; and
if the halt position is after the first scan and before the second scan or in the second scan, resume the second scan from a start position of the second scan.

2. The apparatus of claim 1, wherein the scans are different one another.

3. The apparatus of claim 2, the apparatus further comprising;
a rotating frame configured to rotatably support an X-ray tube configured to generate X-rays and an X-ray detector configured to detect X-rays transmitted through an object on a top; wherein
the scan control unit is configured to determine the scan interruption position as a position of the rotating frame and a position of the top based on the plan and the scan information when the plan is interrupted.

4. An X-ray computed tomography apparatus comprising:
a plan storage unit configured to store a plan for sequentially executing a plurality of scans to acquire a plurality of projection data sets;
a scan information storage unit configured to store scan information including the plurality of projection data sets; and
a scan control unit configured to determine, based on the scan information until an interruption of the scan being executed, a scan interruption position corresponding to a time at which the scan being executed is interrupted and to resume the interrupted scan in the plan from the scan interruption position, wherein the plurality of scans comprises at least one helical scan to acquire one or more of the projection data sets through X-ray irradiation during movement of a top, and wherein the scan control unit is configured to resume the helical scan when the helical scan is interrupted, such that:
if a number of the projection data sets for the helical scan that are stored in the scan information storage unit is equal to or greater than a predetermined margin number, the scan control unit resumes the helical scan from the scan interruption position as of past acquisition of the projection data set for the helical scan that is prior to the latest projection data set by the margin number; and
if the number of the projection data sets for the helical scan that are stored in the scan information storage unit is less than the margin number, the scan control unit determines the scan interruption position as of start of the helical scan as a resumption position, and resumes the helical scan from the resumption position.

5. An X-ray computed tomography apparatus comprising:
a plan storage unit configured to store a plan for sequentially executing a plurality of scans to acquire a plurality of projection data sets;
a scan information storage unit configured to store scan information including the plurality of projection data sets;
a scan control unit configured to determine, based on the scan information until an interruption of the scan being executed, a scan interruption position corresponding to a time at which the scan being executed is interrupted and to resume the interrupted scan in the plan from the scan interruption position; and
an operation unit configured for input of a start time of a specific scan of the plurality of scans, a resumption time of the specific scan after start of the specific scan, and an X-ray irradiation duration in the specific scan, wherein the scan control unit is configured to:
if the input resumption time of the specific scan is between the input start time of the specific scan and a scheduled end time at which the X-ray irradiation duration since the input start time of the specific scan completes, resume the specific scan from a position as of start of the specific scan; and if the input resumption time is on or after the scheduled end time, stop the specific scan.

6. An X-ray computed tomography apparatus comprising:

a plan storage unit configured to store a plan for sequentially executing a plurality of scans to acquire a plurality of projection data sets;

a scan information storage unit configured to store scan information including the plurality of projection data sets; and a scan control unit configured to determine, based on the scan information until an interruption of the scan being executed, a scan interruption position corresponding to a time at which the scan being executed is interrupted and to resume the interrupted scan in the plan from the scan interruption position, wherein the plurality of scans comprises a specific scan and a post scan after the specific scan, wherein the apparatus further comprises an operation unit configured for input of a start time of the specific scan, a start time of the post scan after start of the specific scan, and a duration between the start time of the specific scan and a scheduled start time of the post scan, and wherein the scan control unit is configured to:

if the input start time of the post scan is between the input start time of the specific scan and the scheduled start time, start the post scan at the scheduled start time; and if the input resumption time of the post scan is on or after the scheduled start time, stop the start of the post scan.

* * * * *